(12) United States Patent
Kim et al.

(10) Patent No.: US 10,105,060 B2
(45) Date of Patent: Oct. 23, 2018

(54) BREAST SCANNING APPARATUS USING PHOTOACOUSTIC ULTRASONIC WAVE

(71) Applicant: SAMSUNG ELECTRONICS CO., LTD., Suwon-si (KR)

(72) Inventors: Jong-seok Kim, Hwaseong-si (KR); Sung-chan Kang, Hwaseong-si (KR); Hyung-joo Kim, Seongnam-si (KR); Hyung-jae Shin, Seongnam-si (KR); Yong-seop Yoon, Seoul (KR); Byung-gil Jeong, Anyang-si (KR); Seok-whan Chung, Hwaseong-si (KR); Chang-jung Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 294 days.

(21) Appl. No.: 14/338,507

(22) Filed: Jul. 23, 2014

(65) Prior Publication Data

US 2015/0141795 A1 May 21, 2015

(30) Foreign Application Priority Data

Nov. 20, 2013 (KR) .......................... 10-2013-0141593

(51) Int. Cl.
*A61B 5/00* (2006.01)
*A61B 8/08* (2006.01)
*A61B 8/00* (2006.01)

(52) U.S. Cl.
CPC .......... *A61B 5/0095* (2013.01); *A61B 5/0091* (2013.01); *A61B 5/708* (2013.01); *A61B 8/0825* (2013.01); *A61B 8/42* (2013.01); *A61B 8/406* (2013.01)

(58) Field of Classification Search
CPC .......... A61B 8/00; A61B 5/0095; A61B 8/42; A61B 5/0091; A61B 5/708; A61B 8/0825; A61B 8/406
See application file for complete search history.

(56) References Cited

U.S. PATENT DOCUMENTS

| 5,293,873 | A | 3/1994 | Fang |
| 5,999,836 | A * | 12/1999 | Nelson ................. A61B 5/0091 250/339.02 |
| 6,128,523 | A | 10/2000 | Bechtold et al. |
| 6,292,682 | B1 | 9/2001 | Kruger |
| 2002/0035327 | A1 | 3/2002 | Kruger |
| 2004/0010193 | A1 | 1/2004 | Entrekin |

(Continued)

*Primary Examiner* — Amanda Lauritzen Moher
*Assistant Examiner* — Lisa Kinnard
(74) *Attorney, Agent, or Firm* — Sughrue Mion, PLLC

(57) ABSTRACT

A breast scanning apparatus which uses photoacoustic ultrasonic waves is provided. The breast scanning apparatus includes a body which includes a first hole and a second hole which are horizontally parallel to each other; a first compression plate and a second compression plate, at least one of which is movable in a vertical direction with respect to the body; a first sliding plate and a second sliding plate, which are respectively installed on surfaces of the first compression plate and the second compression plate and are facing each other and are movable in a first direction; a first ultrasonic transducer array in the first compression plate and facing the first sliding plate; and a first laser head in the first compression plate, which is movable in a second direction which is perpendicular to the first direction.

8 Claims, 6 Drawing Sheets

(56) References Cited

U.S. PATENT DOCUMENTS

| | | | |
|---|---|---|---|
| 2004/0182841 A1* | 9/2004 | Denney | B23K 26/032 219/121.78 |
| 2011/0088477 A1* | 4/2011 | Someda | A61B 5/0095 73/641 |
| 2011/0098550 A1 | 4/2011 | Yoda | |
| 2011/0245667 A1* | 10/2011 | Tokita | A61B 5/0091 600/437 |
| 2011/0257530 A1* | 10/2011 | Tokita | A61B 5/0091 600/443 |
| 2013/0039147 A1* | 2/2013 | Witte | A61B 5/0093 367/7 |
| 2013/0109952 A1* | 5/2013 | Motoki | A61B 6/00 600/407 |

* cited by examiner

BREAST SCANNING APPARATUS USING PHOTOACOUSTIC ULTRASONIC WAVE

CROSS-REFERENCE TO RELATED APPLICATIONS

This application claims priority from Korean Patent Application No. 10-2013-0141593, filed on Nov. 20, 2013, in the Korean Intellectual Property Office, the disclosure of which is incorporated herein by reference in its entirety.

BACKGROUND

1. Field

The present disclosure relates to a breast scanning apparatus for precise diagnosis by embodying a functional image in a morphological image by merging an ultrasonic and a photoacoustic image.

2. Description of the Related Art

An ultrasonic probe is used for analyzing morphological features of an organ or a tissue inside a human body by generating an image by transmitting an ultrasonic wave to the human body and receiving echo signals which are reflected from inside the human body.

However, despite improvements in image quality, precision of early-stage cancer diagnosis, such as, for example, a determination of whether a tumor is benign or malignant, is poor due to limits of morphological images based on ultrasonic transmission/reception.

Recently, photoacoustic techniques for producing a functional image by generating ultrasonic waves by irradiating a light (a laser beam) toward a human body tissue, receiving the reflected ultrasonic waves, and measuring light characteristics of the tissue are being developed and applied to medical diagnosis. Research is being actively conducted on techniques for improving precision of diagnosis by simultaneously providing a morphological image and a functional image by combining an ultrasonic image and a photoacoustic image based on an ultrasonic wave system.

However, a conventional probe moves while diagnosing a breast, and thus it is difficult to obtain a clear image.

SUMMARY

Provided are breast scanning apparatuses using photoacoustic ultrasonic wave for obtaining both a photoacoustic image and an ultrasonic image while fixing a probe.

Additional aspects will be set forth in part in the description which follows and, in part, will be apparent from the description, or may be learned by practice of the presented exemplary embodiments.

According to an aspect of one or more exemplary embodiments, a breast scanning apparatus which uses photoacoustic ultrasonic waves is provided. The breast scanning apparatus includes a body which includes a first hole and a second hole which are horizontally parallel to each other; a first compression plate which is disposed at the first hole and a second compression plate which is disposed at the second hole, at least one of the first compression plate and the second compression plate being installed so as to be movable in a vertical direction with respect to the body; a first sliding plate which is installed on a surface of the first compression plate and a second sliding plate which is installed on a surface of the second compression plate so as to face the first sliding plate, each of the first sliding plate and the second sliding plate being movable in a first direction; a first ultrasonic transducer array which is disposed in the first compression plate and which faces the first sliding plate; and a first laser head which is disposed in the first compression plate and is movable in a second direction which is perpendicular to the first direction.

The breast scanning apparatus further includes a second ultrasonic transducer array which is disposed in the second compression plate and which faces the second sliding plate; and a second laser head which is disposed in the second compression plate and which is movable in the second direction.

The breast scanning apparatus further includes a first horizontal moving device configured to cause the first sliding plate to slide with respect to the first compression plate in the second direction; and a second horizontal moving device configured to cause the second sliding plate to slide with respect to the second compression plate in the second direction.

The first horizontal moving device includes a first rack gear arranged on a surface of the first sliding plate which surface is opposite from a surface which faces the second sliding plate; and a first pinion gear arranged to be combined with the first rack gear, and the second horizontal moving device includes a second rack gear arranged on a surface of the second sliding plate which surface is opposite from a surface which faces the first sliding plate; and a second pinion gear arranged to be combined with the second rack gear.

The breast scanning apparatus further includes a first laser head driver configured to scan the first laser head in a horizontal direction, and a second laser head driver configured to scan the second laser head in the horizontal direction.

The first laser head driver includes a first continuous belt which is connected so as to fix the first laser head; a first guiding rod, which is configured to guide a scanning of the first laser head and to facilitate a sliding of the first laser head; and a first driver, which is configured to support and revolve the first continuous belt, and the second laser head driver includes a second continuous belt which is connected so as to fix the second laser head; a second guiding rod, which is configured to guide a scanning of the second laser head and to facilitate a sliding of the second laser head; and a second driver, which is configured to support and revolve the second continuous belt.

The first laser head is configured to irradiate a pulse laser beam which is supplied by a laser generator.

The pulse laser beam has a pulse width which falls in a range of between 1 picosecond and 1000 nanoseconds.

Each of the first ultrasonic transducer array and the second ultrasonic transducer array may include a respective plurality of ultrasonic transducers, and each of the each respective plurality of ultrasonic transducers may include at least one from among a piezoelectric micromachined ultrasonic transducer (pMUT), a capacitive micromachined ultrasonic transducer (cMUT), a magnetic micromachined ultrasonic transducer (mMUT), and an optical ultrasonic detector.

The breast scanning apparatus may further include a signal processor configured to receive a first ultrasonic wave, which is an echo signal, from the first ultrasonic transducer array, and to receive a second ultrasonic wave, which is a photoacoustic wave, from the second ultrasonic transducer array, and to generate a first image, which is a morphological image, and a second image, which is a photoacoustic image; and an image combiner configured to generate a third image by combining the first image with the second image.

The breast scanning apparatus may further include a display device which is configured to display at least one from among the first, second, and third images.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
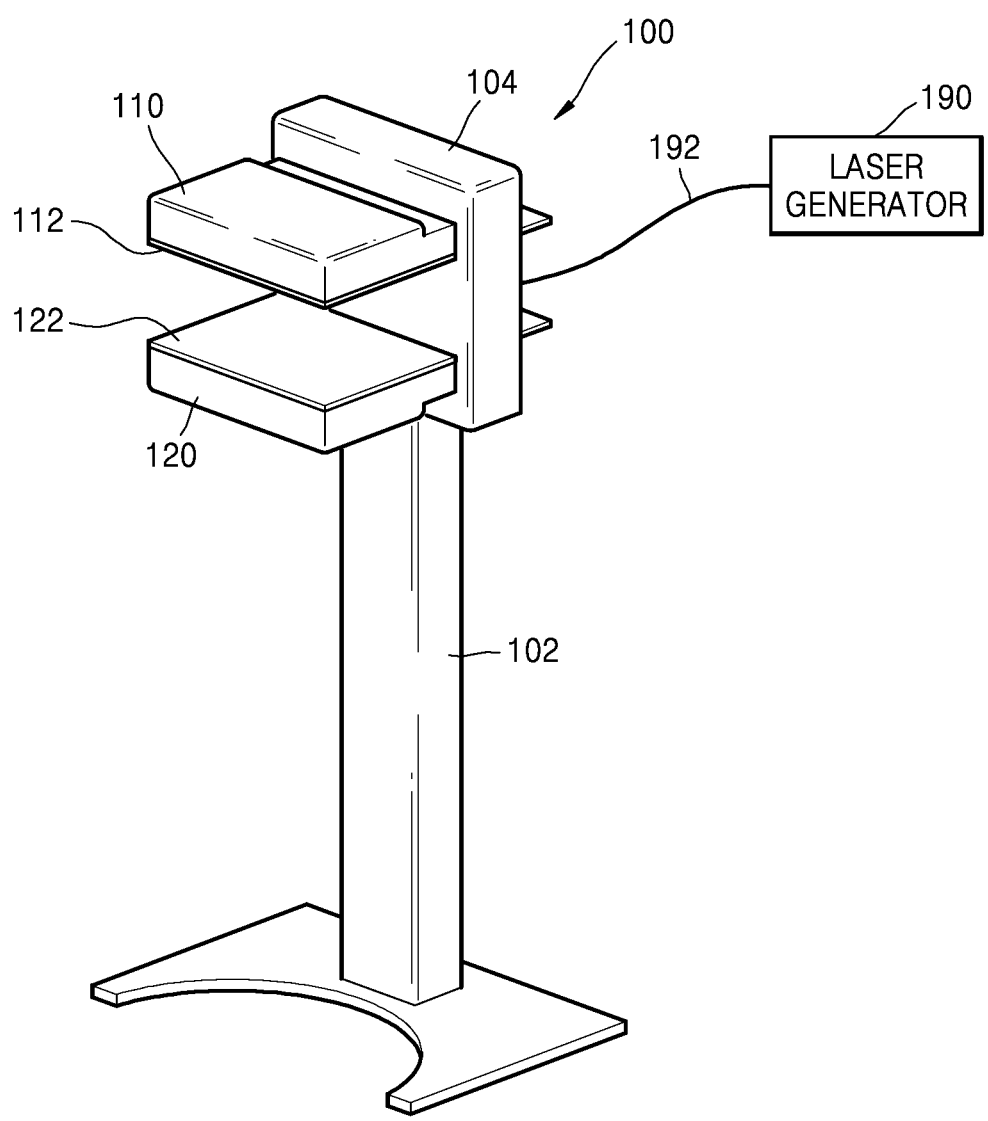
FIG. 1 is a schematic perspective view of a breast scanning apparatus which uses photoacoustic ultrasonic waves, according to one or more exemplary embodiments.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. It will be understood that when a layer, region, or component is referred to as being "formed on" another layer, region, or component, it can be directly or indirectly formed on the other layer, region, or component. That is, for example, intervening layers, regions, or components may be present. Like reference numerals refer to like elements throughout, and detailed descriptions thereof will be omitted.

FIG. 1 is a schematic perspective view of a breast scanning apparatus 100 which uses photoacoustic ultrasonic waves, according to one or more exemplary embodiments.

Referring to FIG. 1, the breast scanning apparatus 100 includes a stand 102, a body 104, and a first compression plate 110 and a second compression plate 120. The first compression plate 110 and the second compression plate 120 are arranged in parallel to each other at the body 104 and disposed to face each other. A first sliding plate 112 and a second sliding plate 122 are arranged on respective surfaces of the first compression plate 110 and the second compression plate 120 so as to face each other.

The stand 102 may include an upper stand (not shown), which is connected to the body 104, and a lower stand (not shown). Vertical heights of the upper stand and the lower stand may be adjusted based on a height of a patient. Detailed descriptions thereof will be omitted.

A laser generator 190 is arranged at a side of the body 104. The laser generator 190 transmits a laser beam to a laser head described below via an optical fiber 192. The compression plates 110 and 120 and the sliding plates 112 and 122 may be formed of a material that transmits a laser beam, such as, for example, a plastic.

Figure 2:
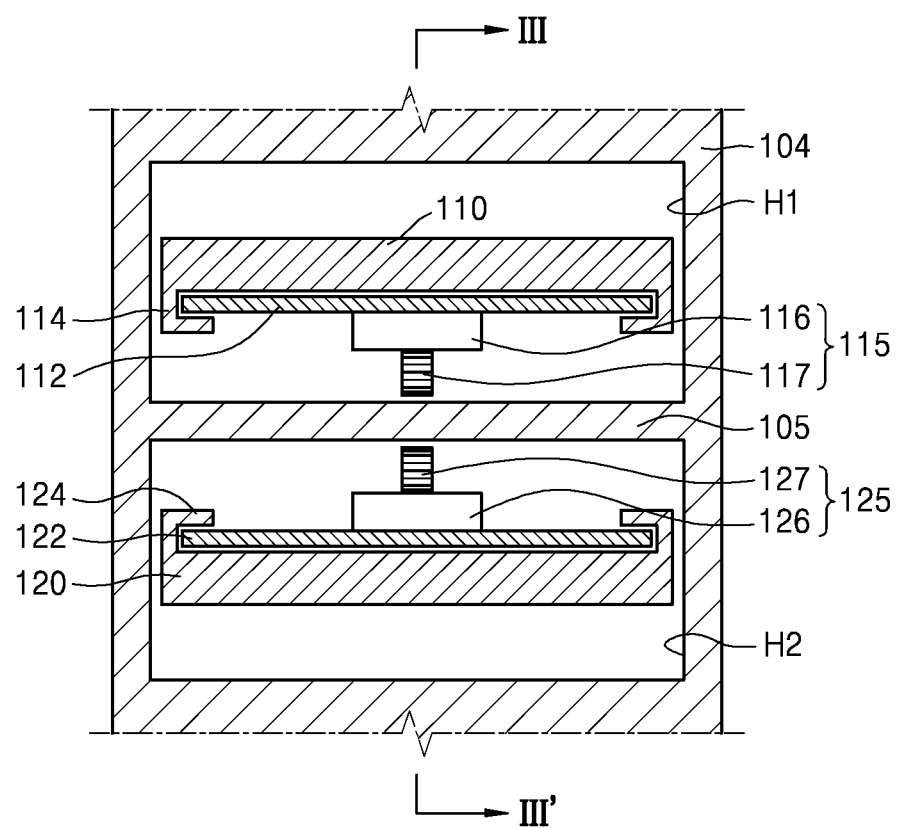
FIG. 2 is a cross-sectional view of a body of the breast scanning apparatus, according to one or more exemplary embodiments.
Figure 3:
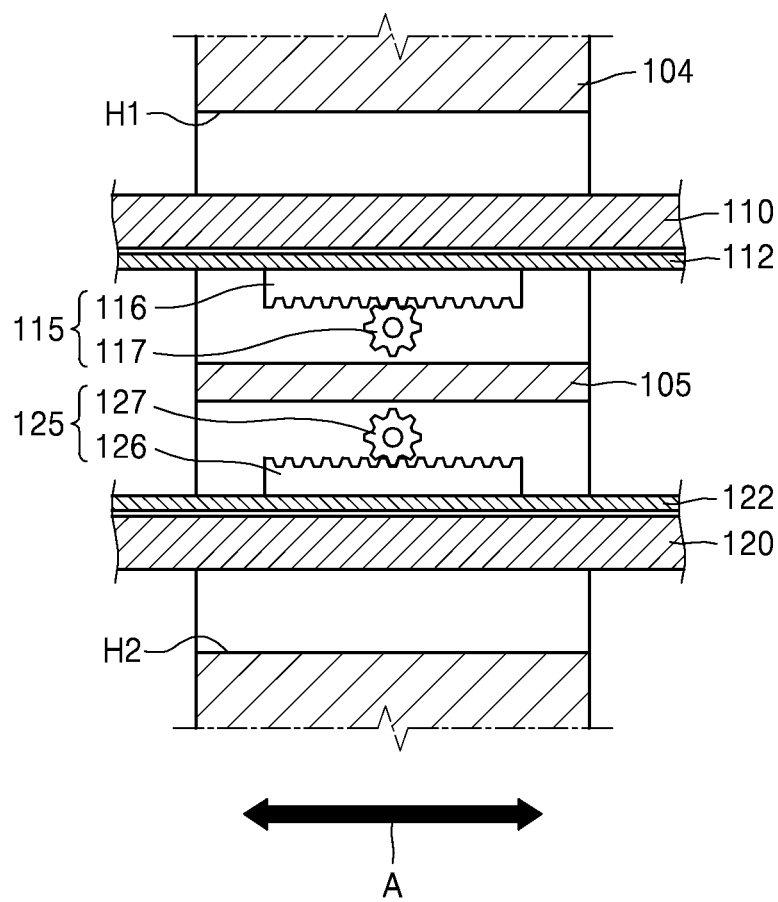
FIG. 3 is a cross-sectional diagram taken along a line III-III' in FIG. 2.

FIG. 2 is a cross-sectional view of the body 104 of the breast scanning apparatus 100. FIG. 3 is a cross-sectional view taken along a line III-III' in FIG. 2.

Referring to FIGS. 2 and 3, a first hole H1 in which the first compression plate 110 vertically moves and a second hole H2 in which the second compression plate 120 vertically moves are formed in the body 104. The first hole H1 and the second hole H2 are formed in parallel to each other, where an intermediate portion 105 of the body 104 is formed between the first hole H1 and the second hole H2. The first compression plate 110 and the second compression plate 120 compress a breast flat by applying pressure to the breast. The first compression plate 110 and the second compression plate 120 may be manually operated. However, the present disclosure is not limited thereto. The first compression plate 110 and the second compression plate 120 may also be driven by a motor.

Alternatively, one of the first compression plate 110 and the second compression plate 120 may be fixed to the body 104, and pressure may be applied to a breast by moving the other of the first compression plate 110 and the second compression plate 120.

The first sliding plate 112 and the second sliding plate 122 closely contact the first compression plate 110 and the second compression plate 120 and slide thereon, respectively. Each of the first sliding plate 112 and the second sliding plate 122 slides in the direction indicated by an arrow A (referring to FIG. 3).

A guiding unit (also referred to herein as a "guide") 114 which supports two opposite ends of the first sliding plate 112 and guides the first sliding plate 112, is formed at two opposite sides of the first compression plate 110. The guiding unit 114 may support the first sliding plate 112 and guide a sliding of the first sliding plate 112. The guiding unit 114 may be formed by extending from the first sliding plate 112. Alternatively, the guiding unit 114 may be a separate member which is arranged so as to be fixed to the first sliding plate 112.

However, the present disclosure is not limited thereto. For example, a groove and a protrusion may be formed at the interface between the first sliding plate 112 and the first compression plate 110, so that the first sliding plate 112 and the first compression plate 110 may be slidably attached to each other. Detailed descriptions thereof will be omitted.

The combination structure between the second compression plate 120 and second sliding plate 122 may be substantially identical to the combination structure between the first compression plate 110 and the first sliding plate 112. For example, a guiding unit (also referred to herein as a "guide") 124 extending from the second compression plate 120 may support two opposite ends of the second sliding plate 122 and facilitate a sliding of the second sliding plate 122.

A first horizontal moving device 115 configured for sliding the first sliding plate 112 with respect to the first compression plate 110 may be arranged on the rear surface of the first sliding plate 112. The first horizontal moving device 115 may include a rack gear 116 which is fixed to the rear surface of the first sliding plate 112 and a pinion gear 117 of which the revolution shaft is fixed to the intermediate portion 105 of the body 104. While the first compression plate 110 is moving and compressing a breast, the rack gear 116 and the pinion gear 117 may be combined with each other.

However, the present disclosure is not limited thereto. For example, the pinion gear 117 may be installed at the body 104 so as to be movable in a vertical direction. Alternatively, the pinion gear 117 may be installed at the intermediate portion 105, such that the revolution shaft of the pinion gear 117 may be movable in a vertical direction, and the pinion gear 117 may be combined with the rack gear 116.

The pinion gear 117 revolves by operation of a motor (not shown), and thus the rack gear 116 is movable in a horizontal direction. Therefore, the first sliding plate 112 is movable in a horizontal direction.

However, the present disclosure is not limited thereto. For example, a worm wheel may be fixedly installed at the rear surface of the first sliding plate 112, a worm gear may be installed at the body 104, the worm wheel may be driven as the worm gear is driven, and thus the first sliding plate 112 may be movable in a horizontal direction.

A second horizontal moving device 125, which is identical to the first horizontal moving device 115 of the first sliding plate 112, may be arranged on the top surface of the second sliding plate 122. For example, the second horizontal moving device 125 may include a rack gear 126 which is installed on the top surface of the second sliding plate 122 and a pinion gear 127 which is installed at the intermediate portion 105 so as to be facing the second sliding plate 122. Detailed descriptions thereof will be omitted.

Figure 4:
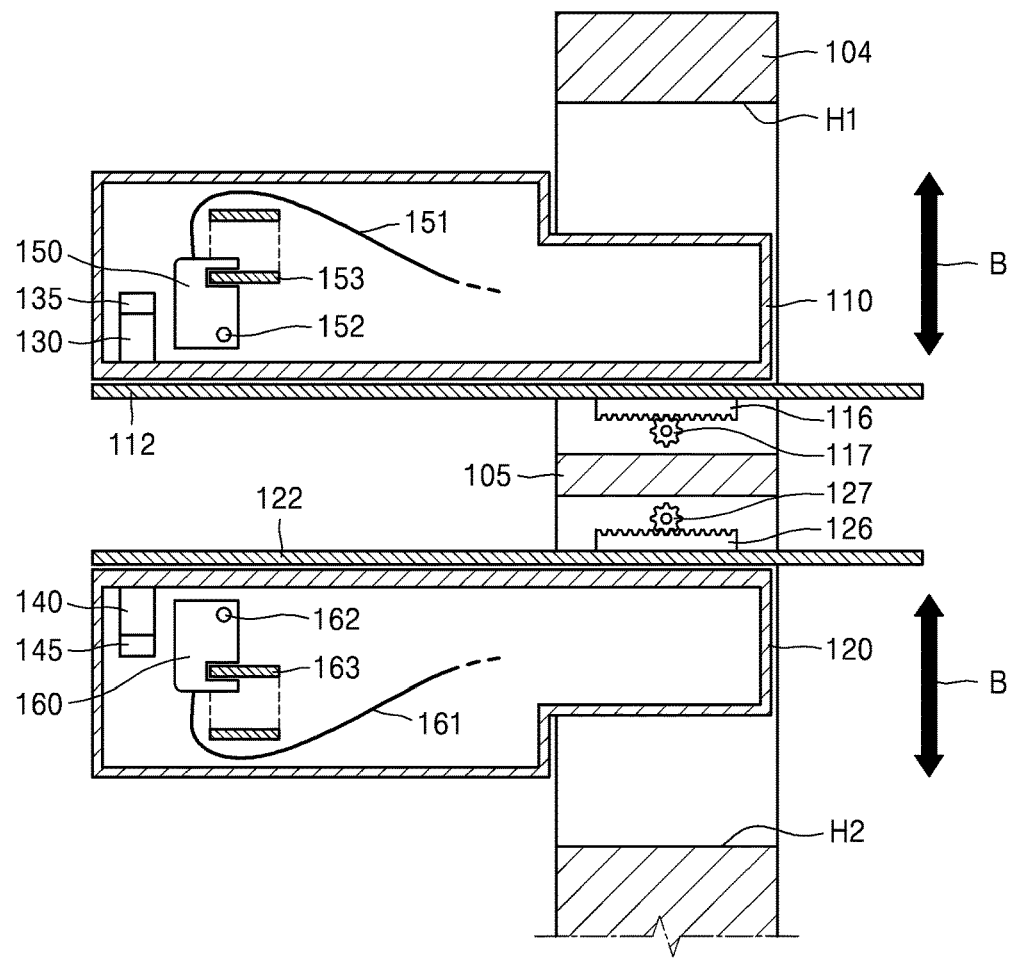
FIG. 4 is a schematic sectional view of the breast scanning apparatus, according to one or more exemplary embodiments.

FIG. 4 is a schematic sectional view which illustrates a portion of the breast scanning apparatus 100, according to one or more exemplary embodiments.

Referring to FIG. 4, the first compression plate 110 and the second compression plate 120 are arranged at the body 104 so as to face each other. The first hole H1 and the second hole H2 are formed in the body 104, so that the first compression plate 110 and the second compression plate 120 move in a vertical direction indicated by an arrow B. When the first compression plate 110 is descended (refer to FIG. 4), the rack gear 116 at the bottom of the first sliding plate 112 may be combined with the pinion gear 117, and the rack gear 116 may be detached from the pinion gear 117 as the first compression plate 110 ascends. In the same aspect, regarding the second compression plate 120, the rack gear 126 and the pinion gear 127 may be combined with each other or detached from each other. In this case, the revolution shafts of the pinion gears 117 and 127 are fixed to the intermediate portion 105.

However, the present disclosure is not limited thereto. While the pinion gears 117 and 127 are combined with the rack gears 116 and 126, the revolution shafts of the pinion gears 117 and 127 may be movable in a vertical direction in conjunction with the compression plates 110 and 120.

In the first compression plate 110, a first ultrasonic transducer array 130 which faces the first sliding plate 112 is arranged. The first ultrasonic transducer array 130 includes at least a plurality of ultrasonic transducers which are arranged in a line. An ASIC substrate 135 which is configured for driving the first ultrasonic transducer array 130 is arranged on the first ultrasonic transducer array 130.

In the second compression plate 120, a second ultrasonic transducer array 140 which faces the second sliding plate 122 is arranged. The second ultrasonic transducer array 140 includes a plurality of ultrasonic transducers which are arranged in a line. An ASIC substrate 145 which is configured for driving the second ultrasonic transducer array 140 is arranged on the second ultrasonic transducer array 140.

A first laser head 150 is arranged at a side of the first ultrasonic transducer array 130. The first laser head 150 is connected to a first optical fiber 151. The first optical fiber 151 receives a laser beam from a laser generator (i.e., item 190 of FIG. 1) and transmits the laser beam to the first laser head 150. A second laser head 160 is arranged at a side of the second ultrasonic transducer array 140. The second laser head 160 is connected to a second optical fiber 161. The second optical fiber 161 receives a laser beam from a laser generator (i.e., item 190 of FIG. 1) and transmits the laser beam to the second laser head 160. Each of the first laser head 150 and the second laser head 160 may include a respective collimating lens which is configured for concentrating a transmitted laser beam.

The laser generator 190 may be configured to generate a solid pulse laser, e.g., Nd:YAG pulse laser. A laser beam pulse width of the laser generator 190 may be measurable in nanoseconds or picoseconds, and thus, the laser beam pulse width may fall within a range of between 1 picosecond and 1000 nanoseconds.

However, the present disclosure is not limited thereto. For example, the second ultrasonic transducer array 140 and the second laser head 160 may be omitted.

Figure 5:
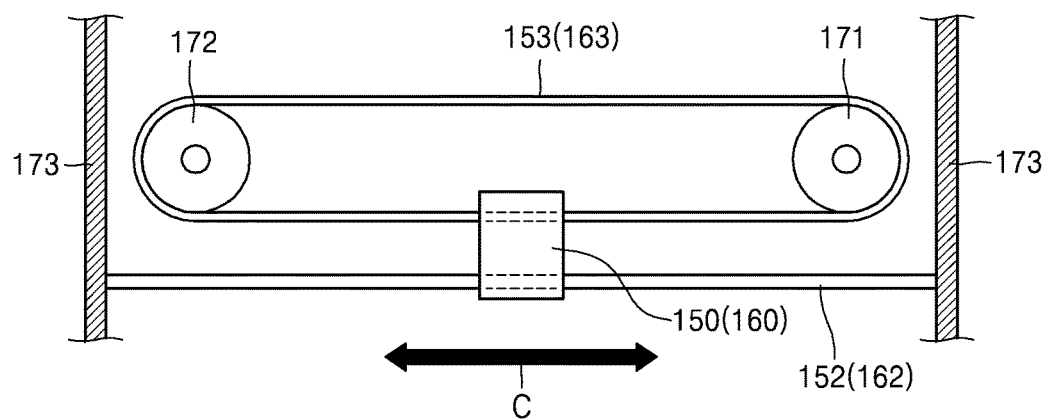
FIG. 5 is a schematic view of a laser head driving unit, according to one or more exemplary embodiments.

FIG. 5 is a schematic view of a laser head driving unit, according to one or more exemplary embodiments.

Referring to FIGS. 4 and 5, the first laser head 150 and the second laser head 160 are respectively arranged at first sides of the first ultrasonic transducer array 130 and the second ultrasonic transducer array 140. A lower portion of each of the first laser head 150 and the second laser head 160 is slidably fixed by guiding rods 152 and 162, respectively. An upper portion of each of the first laser head 150 and the second laser head 160 is fixed to a respective one of continuous belts 153 and 163. The continuous belts 153 and 163 are wound around the driving roll 171 and the driven roll 172 and are supported thereby. As the driving roll 171 revolves, the first laser head 150 and the second laser head 160 may move back and forth in the direction indicated by an arrow C. The direction indicated by the arrow C is perpendicular to the direction in which the first sliding plate 112 and the second sliding plate 122 are movable (the direction indicated by the arrow A in FIG. 3). The driving roll 171 and the driven roll 172 constitute a driving unit (also referred to herein as a "driver") which is configured for driving the continuous belts 153 and 163.

The two opposite ends of the guiding rods 152 and 162 are fixed by the supporting units (also referred to herein as "supports") 173. The supporting units 173 may be fixed to the first compression plate 110 and the second compression plate 120, respectively. However, the present disclosure is not limited thereto. For example, guiding rods 152 and 162 may be fixed to respective surfaces of the first compression plate 110 and the second compression plate 120.

The rotation shaft of the driving roll 171 and the rotation shaft of the driven roll 172 may be fixed by the respective corresponding compression plates 110 and 120. Detailed descriptions thereof will be omitted.

In lieu of the driving roll 171 and the driven roll 172, a driving gear and a driven gear may be used, and gear teeth may be formed at the continuous belts 153 and 163.

Each transducer of the first ultrasonic transducer array 130 and the second ultrasonic transducer array 140 may include one from among a piezoelectric micromachined ultrasonic transducer (pMUT), a capacitive micromachined ultrasonic transducer (cMUT), a magnetic micromachined ultrasonic transducer (mMUT), and an optical ultrasonic detector.

Figure 6:
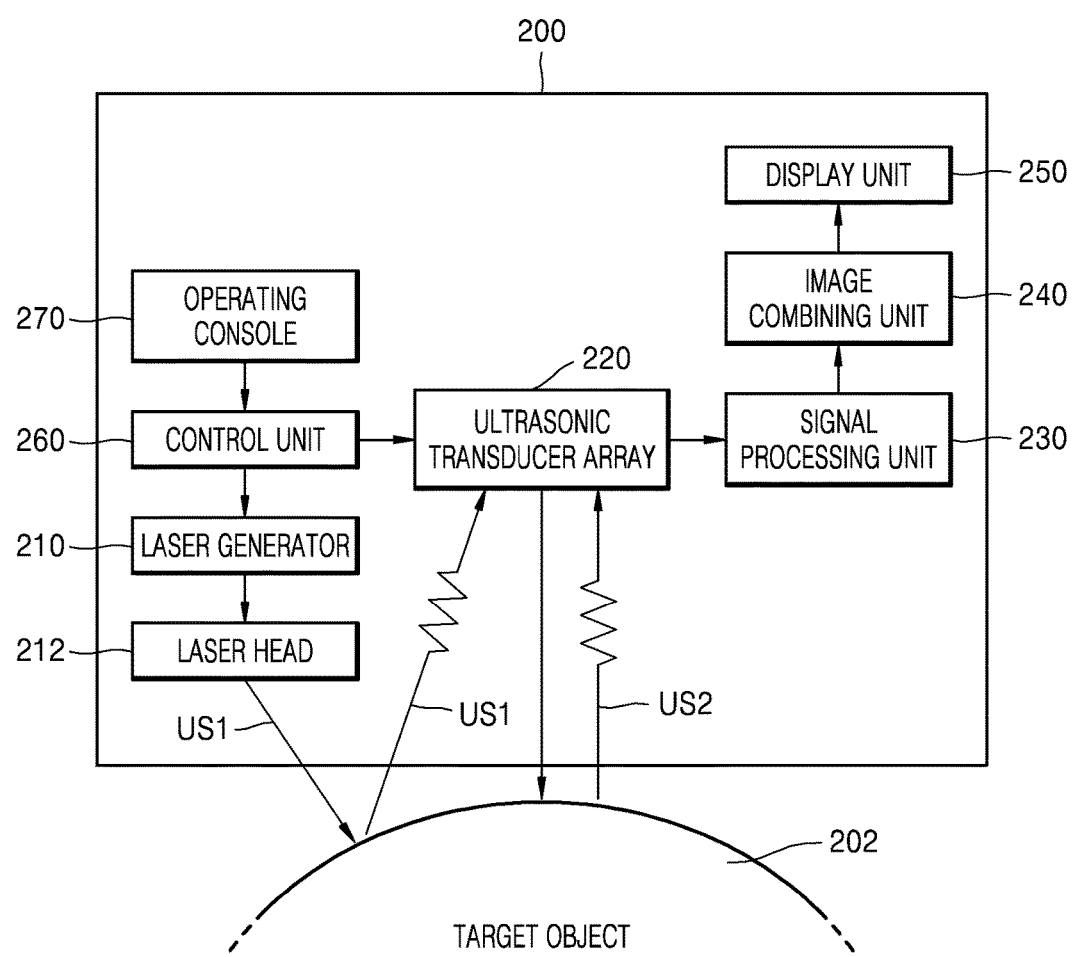
FIG. 6 is a schematic block diagram which illustrates a configuration of a breast scanning apparatus which uses photoacoustic ultrasonic waves, according to one or more exemplary embodiments.

FIG. 6 is a schematic block diagram which illustrates a configuration of a breast scanning apparatus 200 which uses photoacoustic ultrasonic waves, according to one or more exemplary embodiments.

Referring to FIG. 6, the breast scanning apparatus 200 includes a laser generator 210 configured for irradiating a laser beam to a target object 202, which is a breast, and an ultrasonic transducer array 220, which is configured for transmitting a first ultrasonic wave US1 to the target object 202 and for receiving a reflection of the first ultrasonic wave US1, which is an echo signal, from the target object 202.

A laser beam emitted by the laser generator 210 is transmitted to a laser head 212 via an optical fiber, and the laser beam from the laser head is irradiated 212 on a tissue inside the target object 202. The tissue inside the target object 202, e.g., a blood vessel, features a relatively high laser beam absorption quality. Therefore, thermal expansion and contraction occur by the laser beam, thereby generating a second ultrasonic wave US2, which is a photoacoustic wave. The second ultrasonic wave US2 is received by the ultrasonic transducer array 220.

The laser generator 210 may generate a laser beam for inducing the target object 202 to generate the second ultrasonic wave US2 in a form of pulses. For example, the laser generator 210 may be a solid pulse laser, and laser beam pulse width thereof may be measurable in nanoseconds or picoseconds, i.e., the laser beam pulse width may fall within a range of between 1 picosecond and 1000 nanoseconds.

The ultrasonic transducer array 220 corresponds to the first ultrasonic transducer array 130 and the second ultrasonic transducer array 140 as illustrated in FIG. 4.

The ultrasonic transducer array 220 is driven according to control signals which are received from the operating console 270 and the control unit (also referred to herein as a "controller") 260, transmits the first ultrasonic wave US1 to the target object 202, and receives the reflection of the first ultrasonic wave US1 reflected by the target object 202.

The reflection of the first ultrasonic wave US1 and the second ultrasonic wave US2 which are received by the ultrasonic transducer array 220 are converted into electric signals. The electric signals are transmitted to a signal processing unit (also referred to herein as a "signal processor") 230, and the signal processing unit 230 generates a first image by processing electric signals which correspond to the first ultrasonic wave US1. The first image is a morphological image and is an ultrasonic image. Furthermore, the signal processing unit 230 generates a second image by processing electric signals which correspond to the second ultrasonic wave US2. The second image is a functional image and is a photoacoustic image.

The image combining unit (also referred to herein as an "image combiner") 240 generates a third image by combining the first image with the second image. The first image and the second image may be combined with each other at a particular location of the target object 202. The combined image may be a morphological image with respect to the first image, to which the second image reflects properties of a tissue which corresponds to a location in the first image is combined. Because techniques for combining a plurality of images are known in the art, detailed descriptions thereof will be omitted.

A display unit (also referred to herein as a "display device" and/or as a "display") 250 displays the third image which is generated by the image combining unit 240. The display unit 250 may display the first image and/or the second image on demand. Alternatively, the display unit 250 may simultaneously display at least two from among the first, second, and third images.

The control unit 260 controls components of an ultrasonic device 200 based on to user instructions which are received via the operating console 270. The control unit 260 may be embodied as a microprocessor, for example. The operating console 270 receives data which is input by a user. The operating console 270 may include any one or more of a control panel, a keyboard, a mouse, and/or any other device or component which is suitable for facilitating reception of user input.

Figure 7:
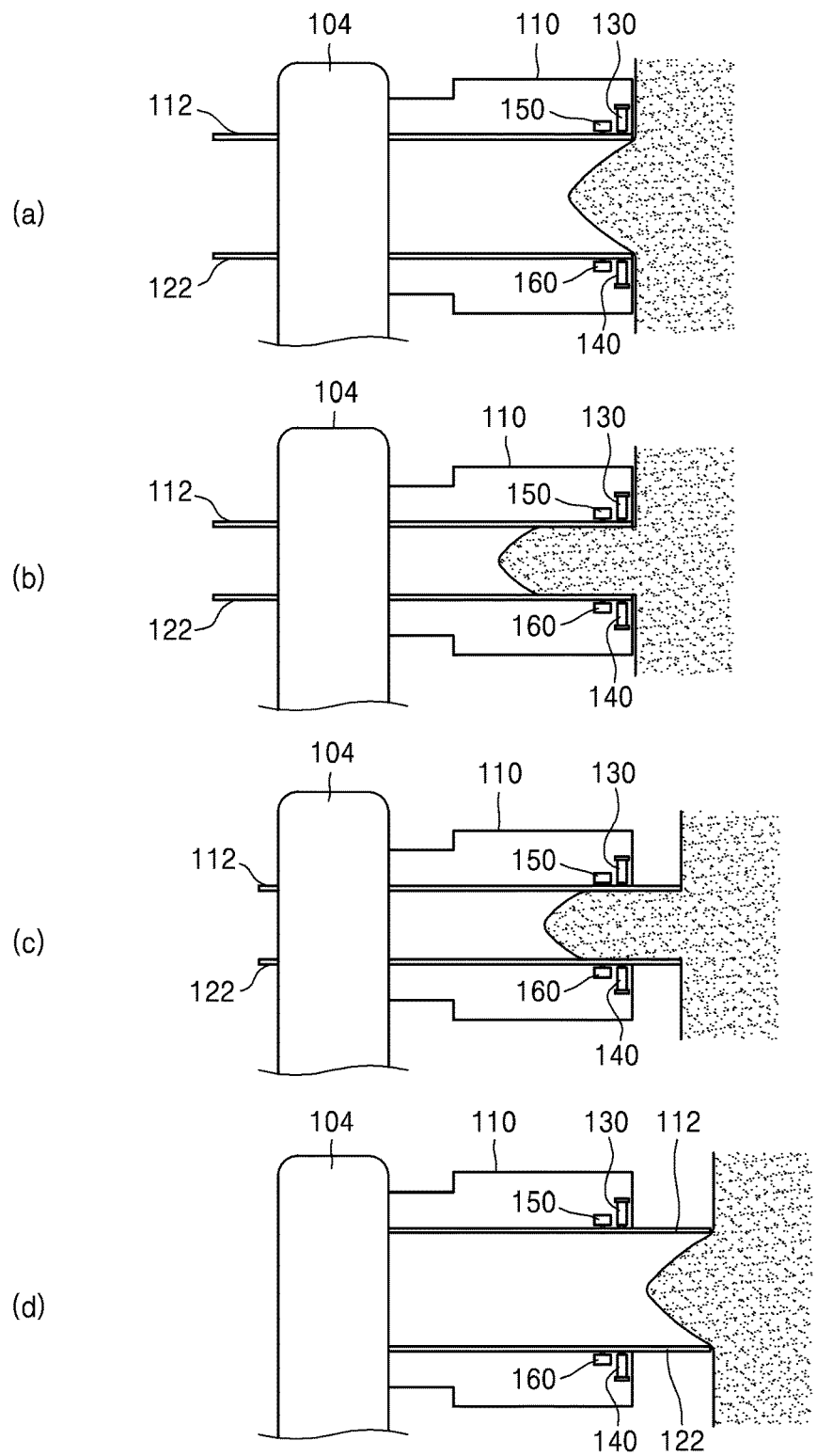
FIG. 7 is a schematic diagram which illustrates a method for operating the breast scanning apparatus which uses photoacoustic waves, according to one or more exemplary embodiments.

FIG. 7 is a schematic diagram which illustrates a method for operating the breast scanning apparatus 100 which uses photoacoustic waves, according to one or more exemplary embodiments. Components substantially identical to those shown in FIGS. 1 through 6 will be denoted by the same reference numerals, and detailed descriptions thereof will be omitted.

Hereinafter, a method for operating the breast scanning apparatus 100 will be described with reference to FIGS. 1 through 7.

First, referring to the topmost drawing, which is labeled (a) in FIG. 7, a breast is positioned between the first compression plate 110 and the second compression plate 120.

Referring to the second drawing, which is labeled (b) in FIG. 7, the first compression plate 110 and the second compression plate 120 are pressed toward each other. Therefore, the first compression plate 110 and the second compression plate 120 compress the breast at a constant pressure. While in this state, the first ultrasonic transducer array 130 and the second ultrasonic transducer array 140 transmit a first ultrasonic wave into the breast and then receive the first ultrasonic wave reflected by the breast via the first ultrasonic transducer array 130 and the second ultrasonic transducer array 140. Next, while the driving roll 171 is being operated, laser beams from the first laser head 150 and the second laser head 160 linearly scan the breast. Photoacoustic ultrasonic waves (i.e., second ultrasonic waves) which are emitted from inside the breast during the scanning, are received by the first ultrasonic transducer array 130 and the second ultrasonic transducer array 140.

Referring to the third drawing, which is labeled (c) in FIG. 7, the pinion gears 117 and 127 of the first and second horizontal moving devices 115 and 125 are driven. Therefore, the first sliding plate 112 and the second sliding plate 122 slide from the compression plates 110 and 120 toward a patient by a predetermined distance. Here, the first ultrasonic transducer array 130 and the second ultrasonic transducer array 140 are at fixed positions. Therefore, the patient moves back, and thus a portion of the breast which is relatively far from the patient is diagnosed. In particular, the line scanning operation for receiving the first ultrasonic wave and the second ultrasonic wave is repeated.

Referring to the bottom drawing, which is labeled (d) in FIG. 7, the sliding plates 112 and 122 are continuously moved toward the patient and the line scanning operation as described above is repeatedly performed. When the breast is completely scanned, the first compression plate 110 and the second compression plate 120 are moved away from each other, thereby releasing the breast from the compression thereof. Next, the pinion gears 117 and 127 of the first and second horizontal moving devices 115 and 125 are driven to move the first sliding plate 112 and the second sliding plate 122 back to their original locations as shown in drawing (a) of FIG. 7.

In the operations shown in drawings (b) and (c) of FIG. 7, the first ultrasonic wave and the second ultrasonic wave received by the first ultrasonic transducer array 130 and the first laser head 150 are input to the signal processing unit 230. The signal processing unit 230 generates a first image by processing first electric signals which correspond to the first ultrasonic wave. The first image is a morphological image. The signal processing unit 230 generates a second image by processing second electric signals which correspond to the second ultrasonic wave. The second image is a photoacoustic image.

Because operations of the image combining unit 240, the display unit 250, the control unit 260, and the operating console 270 are described above with reference to FIG. 6, detailed descriptions thereof will be omitted.

A breast scanning apparatus which uses photoacoustic ultrasonic waves according to exemplary embodiments provides a combination of a morphological ultrasonic image and a photoacoustic ultrasonic image, thereby facilitating an improved accuracy and an improved precision in a diagnosis of breast cancer.

Because an operator may perform breast diagnosis instead of a doctor, the overall throughput may increase.

Furthermore, because laser beams are irradiated from two opposite directions, the resulting amount of laser beams reaching a breast tissue may be increased, and thus, a strong ultrasonic signal may be obtained. Because ultrasonic transducer arrays and laser heads are fixed to a breast scanning apparatus and a diagnosis point of a breast moves as sliding plates move, a probe is not moved, and thus a clear image may be obtained.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A breast scanning apparatus which uses photoacoustic ultrasonic waves, the breast scanning apparatus comprising:
    a body which includes a first hole and a second hole which are horizontally parallel to each other;
    a first compression plate which is disposed at the first hole and a second compression plate which is disposed at the second hole, at least one of the first compression plate and the second compression plate being installed so as to be movable in a direction connecting the first hole and the second hole;
    a first sliding plate which is installed on a surface of the first compression plate and a second sliding plate which is installed on a surface of the second compression plate so as to face the first sliding plate, each of the first sliding plate and the second sliding plate being movable in a first direction which is parallel to the surface thereof and perpendicular to the direction connecting the first hole and the second hole;
    a first ultrasonic transducer array which is disposed inside the first compression plate and which faces the first sliding plate;
    a first laser head which is disposed inside the first compression plate and which is movable in a second direction which is perpendicular to the first direction;
    a first horizontal moving device configured to cause the first sliding plate to slide on the surface of the first compression plate in the first direction; and
    a second horizontal moving device configured to cause the second sliding plate to slide on the surface of the second compression plate in the first direction.

2. The breast scanning apparatus of claim 1, wherein the first horizontal moving device comprises:
    a first rack gear arranged on a surface of the first sliding plate which surface is opposite from a surface which faces the second sliding plate; and
    a first pinion gear arranged to be combined with the first rack gear,
    and wherein the second horizontal moving device comprises:
    a second rack gear arranged on a surface of the second sliding plate which surface is opposite from a surface which faces the first sliding plate; and
    a second pinion gear arranged to be combined with the second rack gear.

3. The breast scanning apparatus of claim 1, further comprising:
    a second ultrasonic transducer array which is disposed inside the second compression plate and faces the second sliding plate; and
    a second laser head which is disposed inside the second compression plate and which is movable in the second direction.

4. The breast scanning apparatus of claim 3, wherein each of the first ultrasonic transducer array and the second ultrasonic transducer array includes a respective plurality of ultrasonic transducers, and
    each of the each respective plurality of ultrasonic transducers includes at least one from among a piezoelectric micromachined ultrasonic transducer (pMUT), a capacitive micromachined ultrasonic transducer (cMUT), a magnetic micromachined ultrasonic transducer (mMUT), and an optical ultrasonic detector.

5. The breast scanning apparatus of claim 3, further comprising:
    a first laser head driver configured to scan the first laser head in a horizontal direction, and a second laser head driver configured to scan the second laser head in the horizontal direction.

6. The breast scanning apparatus of claim 5, wherein the first laser head driver comprises:
    a first continuous belt which is connected so as to fix the first laser head;
    a first guiding rod, which is configured to guide a scanning of the first laser head and to facilitate a sliding of the first laser head; and
    a first driver, which is configured to support and revolve the first continuous belt, and
    the second laser head driver comprises:
    a second continuous belt which is connected so as to fix the second laser head;
    a second guiding rod, which is configured to guide a scanning of the second laser head and to facilitate a sliding of the second laser head; and
    a second driver, which is configured to support and revolve the second continuous belt.

7. The breast scanning apparatus of claim 1, wherein the first laser head is configured to irradiate a pulse laser beam which is supplied by a laser generator.

8. The breast scanning apparatus of claim 7, wherein the pulse laser beam has a pulse width which falls in a range of between 1 picosecond and 1000 nanoseconds.

* * * * *